United States Patent [19]
Miura et al.

[11] Patent Number: 5,963,316
[45] Date of Patent: *Oct. 5, 1999

[54] METHOD AND APPARATUS FOR INSPECTING A SURFACE STATE

[75] Inventors: Seiya Miura, Isehara; Michio Kohno, Tokyo; Nobuhiro Kodachi, Kawasaki, all of Japan

[73] Assignee: Canon Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/954,879

[22] Filed: Oct. 21, 1997

Related U.S. Application Data

[60] Continuation of application No. 08/674,709, Jul. 2, 1996, abandoned, which is a division of application No. 08/067,105, May 26, 1993, abandoned.

[30] Foreign Application Priority Data

May 29, 1992 [JP] Japan .................................... 4-164228

[51] Int. Cl.[6] .................................................. G01N 21/88
[52] U.S. Cl. ............................... 356/237.3; 356/239.8; 356/237.5; 250/559.09
[58] Field of Search ........................... 356/237, 239, 356/338, 429, 430, 431, 369, 364, 445, 73, 237.1, 237.2, 237.3, 237.5, 239.8; 250/562, 563, 561, 559, 571, 572, 225, 559.09, 559.41, 559.16

[56] References Cited

U.S. PATENT DOCUMENTS

| | | | |
|---|---|---|---|
| 4,460,273 | 7/1984 | Koizumi et al. | 356/237.2 |
| 4,614,427 | 9/1986 | Koizumi et al. | 356/237.1 |
| 4,669,875 | 6/1987 | Shiba et al. | 356/237.3 |
| 4,669,885 | 6/1987 | Ina | 356/443 |
| 4,764,007 | 8/1988 | Hirvonen | 356/237.2 |
| 4,795,911 | 1/1989 | Kohno et al. | 250/572 |
| 4,831,274 | 5/1989 | Kohno et al. | 250/563 |
| 4,866,975 | 9/1989 | Hopkins | 72/448 |
| 4,886,975 | 12/1989 | Murakami et al. | 356/237.2 |
| 4,893,932 | 1/1990 | Knollenberg | 356/369 |
| 4,965,454 | 10/1990 | Yamauchi et al. | 356/237.3 |
| 4,999,511 | 3/1991 | Kohno | 356/237.3 |
| 5,017,798 | 5/1991 | Murakami et al. | 250/572 |
| 5,105,092 | 4/1992 | Natsubori et al. | 250/572 |
| 5,162,867 | 11/1992 | Kohno | 356/237.5 |
| 5,245,403 | 9/1993 | Kato et al. | 356/369 |
| 5,359,407 | 10/1994 | Suzuki et al. | 356/237.2 |
| 5,365,330 | 11/1994 | Hagiwara | 356/237.3 |
| 5,381,225 | 1/1995 | Kohno | 356/237.5 |
| 5,585,918 | 12/1996 | Takeuchi et al. | 356/237.1 |

FOREIGN PATENT DOCUMENTS

| | | |
|---|---|---|
| 57-066345 | 4/1982 | Japan . |
| 62-179641 | 8/1987 | Japan . |
| 62-188943 | 8/1987 | Japan . |

*Primary Examiner*—Hoa Q. Pham
*Attorney, Agent, or Firm*—Fitzpatrick, Cella, Harper & Scinto

[57] ABSTRACT

A method and apparatus for inspecting a surface state are used to examine first and second surfaces, e.g., two surfaces of a glass substrate on which a device pattern is formed, or one surface of a glass substrate and a pellicle for preventing attachment of foreign particles. When the first surface is illuminated from the first surface side while the second surface is illuminated from the second surface side, the first and second surfaces are illuminated with polarized light beams polarized in directions orthogonal to each other, respectively, and reflectively scattered light from the first surface is detected through an analyzer which intercepts the same polarized light as the polarized light illuminating the second surface. The S/N ratio of examination of the first surface is thereby improved.

5 Claims, 15 Drawing Sheets

PRIOR ART

PRIOR ART

METHOD AND APPARATUS FOR INSPECTING A SURFACE STATE

This application is a continuation of application Ser. No. 08/674,709, filed Jul. 2, 1996, now abandoned, which in turn is a division of application Ser. No. 08/067,105, filed May 26, 1993, now abandoned.

BACKGROUND OF THE INVENTION

1. Field of the Invention

This invention relates to a method and an apparatus for inspecting the state of a surface of an object and, more particularly, to a method and an apparatus for determining the existence/non-existence of defects and foreign particles on a reticle (photomask) and a pellicle, for protecting the reticle from foreign particles. The reticle and pellicle are used when a device, such as a semiconductor memory, a liquid crystal display, a solid-state image pickup device, or a magnetic head, is manufactured.

2. Description of the Related Art

FIG. 1 shows an example of an apparatus for inspecting foreign particles. A pellicle 3 attached to a pellicle frame 4 is provided under a lower surface 2a of a reticle 1 on which a circuit pattern is formed. The pellicle 3 serves to prevent foreign particles or the like from attaching to the lower surface 2a. The apparatus is arranged to examine foreign particles and defects on the lower surface 2a, the pellicle 3 and an upper surface 2b (blank) on which no pattern is formed.

The lower surface 2a, the pellicle 3 and the upper surface 2b are scanned with scanning light beams 5a and 5b from a scanning optical system (not shown) in a direction perpendicular to the projected plane of FIG. 1, while the reticle 1 is moved in the direction of arrow $S_1$. Scattered light caused by foreign particles or the like on the lower surface 2b during this optical scanning is introduced into a photodetector 6a through a light receiving system 52 having a condenser lens (not shown). The scattered light caused by foreign particles or the like on the pellicle 3 during this optical scanning is introduced into a photodetector 6c through a light receiving system 51 having a cylindrical lens 51c and an optical fiber 10c. The scattered light caused by foreign particles or the like on the upper surface 2b during this optical scanning is introduced into a photodetector 6b through a light receiving system 53 having a cylindrical lens 53b and an optical fiber 10b.

FIG. 2 is a diagram showing a problem of the apparatus shown in FIG. 1. In FIG. 2, the same components as those shown in FIG. 1 are indicated by the same reference characters. Solid lines 60 indicate scattered light caused at the pellicle 3, dotted lines 61 indicate diffracted light caused by the circuit pattern, and reference characters F' and G' indicate regions irradiated by the scanning light. An angle θi is formed between a center ray of scanning light 5a and the pellicle 3 (surfaces 2a, 2b), and an angle θd' is formed between the optical axis of the light receiving system 51 and the pellicle 3 (surfaces 2a, 2b).

As can be understood from FIG. 2, when scanning light 5a reaches the pellicle frame 4, reflected light caused by the reflection of scanning light 5a upon the pellicle frame 4 travels to the lower surface 2a to cause diffracted light 61 from the irradiated region F', and the diffracted light 61 enters the light receiving system 51. Accordingly, if there is no foreign particle or defect in the irradiated region G', diffracted light from the irradiated region F' is erroneously detected as scattered light from some foreign particle or defect in the irradiated region G'.

Also in the apparatus shown in FIG. 1, when scanning light 5a, which is obliquely irradiating the reticle 1 from below reaches the pellicle frame 4 or the lower surface 2a, a part of scattered light from the pellicle frame 4 and diffracted light from the circuit pattern on the lower surface 2a enters the light receiving system 53 provided above the reticle 1. If there is no foreign particle or defect on the upper surface 2b, scattered light from the pellicle frame 4 or diffracted light from the circuit pattern on the lower surface 2a is erroneously detected as scattered light from some foreign particle or defect on the upper surface 2b.

FIG. 3 is a diagram showing another problem of the apparatus for examining a foreign particle or the like on a reticle. In FIG. 3, the same components as those shown in FIG. 1 are indicated by the same reference characters. Pellicles 3a and 3b, pellicle frames 4a and 4b, and light receiving systems 80 and 90, are for both receiving scattered light from the reticle upper surface 2b, and the pellicle 3b, which protects the upper surface 2b, and for introducing the scattered light into corresponding photodetectors 80 and 90. The light receiving systems 6a and 6b have cylindrical lenses 61a and 61b, lens barrels 62a and 62b, field stops 64a and 64b, and optical fibers 10a and 10b, respectively.

As can be understood from FIG. 3, when reflected light caused by the reflection on the upper surface 2b of scanning light 5b, which is obliquely irradiating the reticle 1 from above, reaches a point P on the pellicle frame 4b, scattered light from the point P enters the light receiving systems 80 and 90, and is erroneously detected as scattered light from some foreign particle or a defect on the upper surface 2b or the pellicle 3b, even though there is no foreign particle or defect on the upper surface 2b or the pellicle 3b.

SUMMARY OF THE INVENTION

In view of the above-described problems, an object of the present invention is to provide a method and apparatus for correctly inspecting a surface state.

According to one aspect of the present invention, there is provided a method of optically inspecting a first surface and a second surface superposed on and spaced apart from each other comprising the steps of, illuminating the first and second surfaces with light beams polarized in different directions, respectively, and detecting light from the first surface through an analyzer.

According to another aspect of the present invention, there is provided a method of optically inspecting a first surface and a second surface superposed on and spaced apart from each other, comprising the steps of, illuminating the first and second surfaces with light beams polarized in different directions, respectively, and detecting light from the first surface through an analyzer which substantially blocks polarized light with the same polarization as the polarized light illuminating the second surface.

According to yet another aspect of the present invention, there is provided a method of optically inspecting a first surface and a second surface superposed on and spaced apart from each other, a device pattern being formed on the second surface, the first surface being illuminated from the first surface side, the second surface being illuminated from the second surface side, the method comprising the steps of, illuminating the first and second surfaces with light beams polarized in directions orthogonal to each other, respectively, and detecting reflected, scattered light from the first surface through an analyzer which substantially blocks polarized light with the same polarization as the polarized light illuminating the second surface. Preferably, the first surface is formed of a surface of a pellicle which covers a surface of a substrate opposite to another surface of the substrate that corresponds to the second surface.

According to still another aspect of the present invention, there is provided a method in which a light beam is obliquely incident upon a second surface through a first surface, the first and second surfaces being superposed on each other with a frame interposed therebetween and in which light from the first surface is detected, the method comprising the steps of, setting a detection optical axis at an angle to the first surface, which is smaller than an angle formed between the obliquely-incident light beam and the first surface, and detecting light traveling along the detection optical axis.

According to a further aspect of the present invention, there is provided a method in which a light beam is obliquely incident upon a substrate through a foreign particle protective film stretched on a frame placed on the substrate, wherein scattered light from the foreign particle protective film is detected while the obliquely-incident light beam and the substrate are moved relative to each other, the method comprising the steps of, setting a detection optical axis at an angle to a surface of the substrate smaller than an angle formed between the obliquely-incident light beam and the surface of the substrate, and detecting light traveling along the detection optical axis.

According to still a further aspect of the present invention, there is provided a method in which a light beam is obliquely incident upon a substrate through a foreign particle protective film stretched on a frame, which is placed on the substrate and in which scattered light from the foreign particle protective film is detected while the obliquely-incident light beam and the substrate are moved relative to each other, the method comprising the steps of, setting a detection optical axis at an angle to a surface of the film smaller than an angle formed between the obliquely-incident light beam and the surface of the film such that forwardly-scattered reflected light from the foreign particle protective film can be detected, and detecting the forwardly-scattered reflected light traveling along the detection optical axis.

According to still a further aspect of the present invention, there is provided a method of detecting light from at least one of a first surface and a second surface superposed on each other with a frame interposed therebetween, the method comprising the steps of, blocking by a first light shield member, and blocking scattered light caused by incidence of light from the frame upon the first light shield member by a second light shield member.

According to still a further aspect of the present invention, there is provided a method in which a light beam is obliquely incident upon a substrate through a foreign particle protective film stretched on a frame placed on the substrate, and in which scattered light from at least one of the substrate and the foreign particle protective film is detected while the obliquely-incident light beam and the substrate are moved relative to each other, the method comprising the steps of, blocking by a first light shield member, and blocking scattered light caused by incidence of light from the frame upon the first light shield member by a second light shield member.

According to still a further aspect of the present invention, there is provided a surface state inspection apparatus used to optically examine a first surface and a second surface superimposed on and spaced apart from each other, the apparatus comprising means for illuminating the first and second surfaces with light beams polarized in different directions, respectively, means for detecting light from the first surface through an alanyzer, and means for detecting light from the second surface.

According to yet another aspect of the present invention, there is provided a surface state inspection apparatus used to optically examine a first surface and a second surface superimposed on and spaced apart from each other, the apparatus comprising means for illuminating the first and second surfaces with light beams polarized in different directions, respectively, means for detecting light from the first surface through an alanyzer which substantially intercepts polarized light with the same polarization as the polarized light illuminating the second surface, and means for detecting light from the second surface.

According to still a further aspect of the present invention, there is provided a surface state inspection apparatus used to optically examine a first surface and a second surface superimposed on and spaced apart from each other, a device pattern being formed on the second surface, the apparatus comprising illumination means for illuminating the first and second surfaces with light beams polarized in directions orthogonal to each other, respectively, the illumination means illuminating the first surface from the first surface side and illuminating the second surface from the second surface side, means for detecting reflectively scattered light from the first surface with an alanyzer which substantially intercepts polarized light with the same polarization as the polarized light illuminating the second surface, and means for detecting reflectively scattered light from the second surface.

According to yet another aspect of the present invention, there is provided a surface state inspection apparatus which uses a light beam obliquely incident upon a second surface through a first surface, the first and second surfaces being superimposed on each other, and which detects light from the first surface, the apparatus comprising: supply means for supplying the obliquely-incident light, and detection means for detecting scattered light from the first surface, the detection means having an optical axis forming an angle with the first surface, the angle being smaller than an angle formed between the obliquely-incident light beam and the first surface.

According to still a further aspect of the present invention, there is provided a surface state inspection apparatus which uses a light beam obliquely incident upon a substrate through a foreign particle protective film stretched on a frame, which is placed on the substrate, and which detects scattered light from the foreign particle protective film while relatively moving the obliquely-incident light beam and the substrate, the apparatus comprising: supply means for supplying the obliquely-incident light, and detection means for detecting scattered light from the foreign particle protective film, the detection means having an optical axis forming an angle with a surface of the film, the angle being smaller than an angle formed between the obliquely-incident light beam and the surface of the film.

According to yet another aspect of the present invention, there is provided a surface state inspection apparatus which uses a light beam obliquely incident upon a substrate through a foreign particle protective film stretched on a frame placed on the substrate, and which detects scattered light from the foreign particle protective film while relatively moving the obliquely-incident light beam and the substrate, the apparatus comprising: supply means for supplying the obliquely-incident light, and detection means for detecting scattered light from the foreign particle protective film, the detection means having an optical axis forming an angle with a surface of the film, the angle being smaller than an angle formed between the obliquely-incident light beam and the surface of the film, the detection means being arranged to detect forwardly-scattered reflected light from the foreign particle protective film.

According to still a further aspect of the present invention, there is provided a surface state inspection apparatus for detecting light from at least one of a first surface and a second surface superposed on each other with a frame interposed therebetween, the apparatus comprising: illumination means for illuminating the surfaces, and detection means for detecting the light from at least one surface, the detection means comprising a first light shield member for intercepting scattered light from the frame, and a second light shield member for intercepting scattered light caused by incidence of light from the frame upon the first light shield member.

According to yet another aspect of the present invention, there is provided a surface state inspection apparatus which uses a light beam obliquely incident upon a substrate through a foreign particle protective film stretched on a frame which is placed on the substrate, and which detects scattered light from at least one of the substrate and the foreign particle protective film while relatively moving the obliquely-incident light beam and the substrate, the apparatus comprising supply means for supplying the obliquely-incident light, and detection means for detecting scattered light, the detection means comprising a first light shield member for intercepting scattered light from the frame, and a second light shield member for intercepting scattered light caused by incidence of light from the frame upon the first light shield member.

In the above-described methods and apparatuses of the present invention, the examination accuracy can be improved with which the existence/non-existence and/or size of defects and foreign particles on a reticle (photomask) and a pellicle for protecting the reticle, which are used to manufacture a device such as a semiconductor memory, a liquid crystal display, a solid-state image pickup device, a magnetic head or the like, are detected.

According to the present invention, therefore, a device manufacturing method or an exposure apparatus comprising steps or an apparatus which makes it possible to correctly determine whether a reticle (photomask) and a pellicle for protecting the reticle, which are used to manufacture a device such as a semiconductor memory, a liquid crystal display, a solid-state image pickup device, a magnetic head or the like, can be used.

These and other objects, features and advantages of the present invention will become apparent from the following detailed description of preferred embodiments of the invention.

Figure 1:
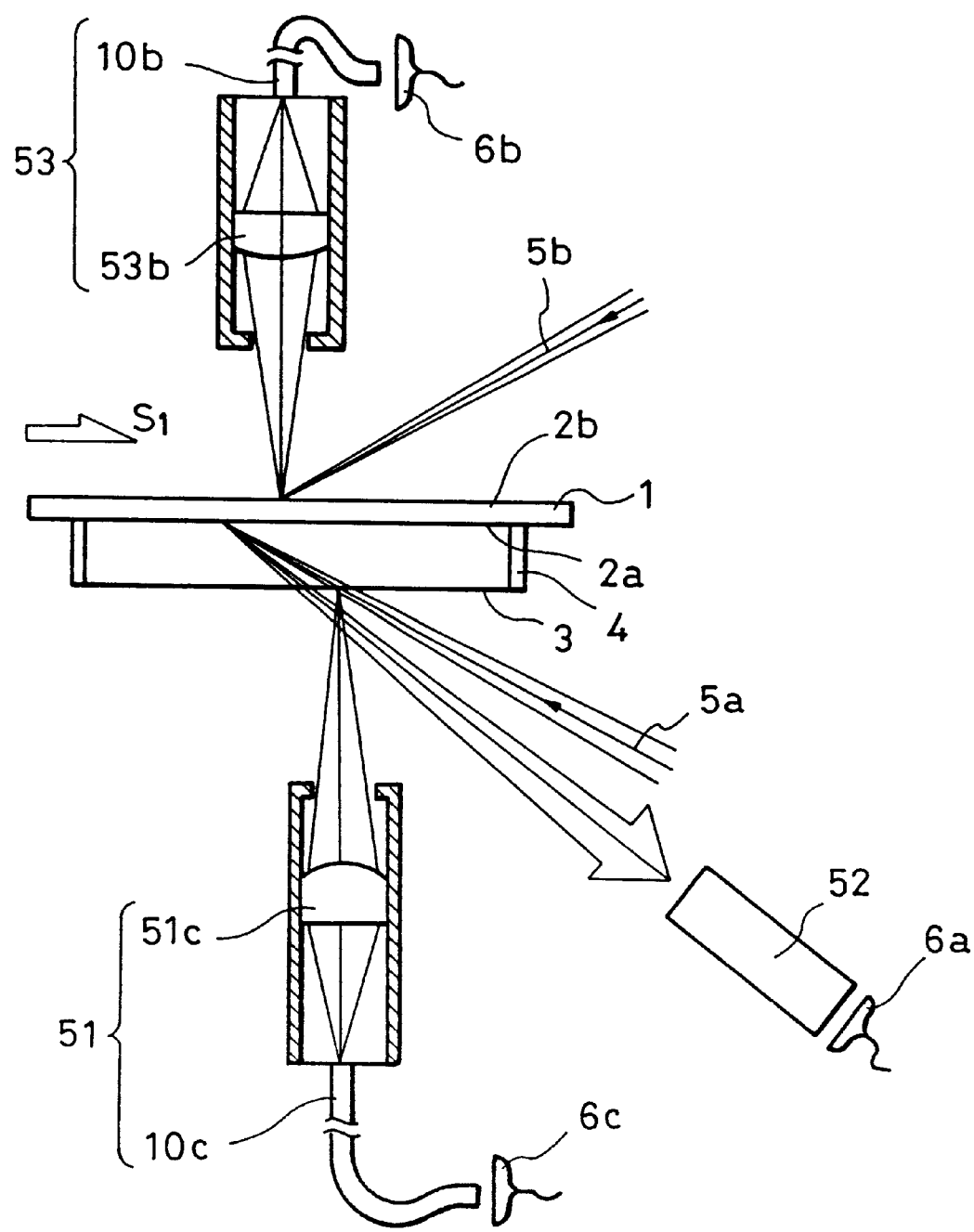
FIG. 1 is a diagram of an example of a conventional foreign particle examination apparatus.
Figure 2:
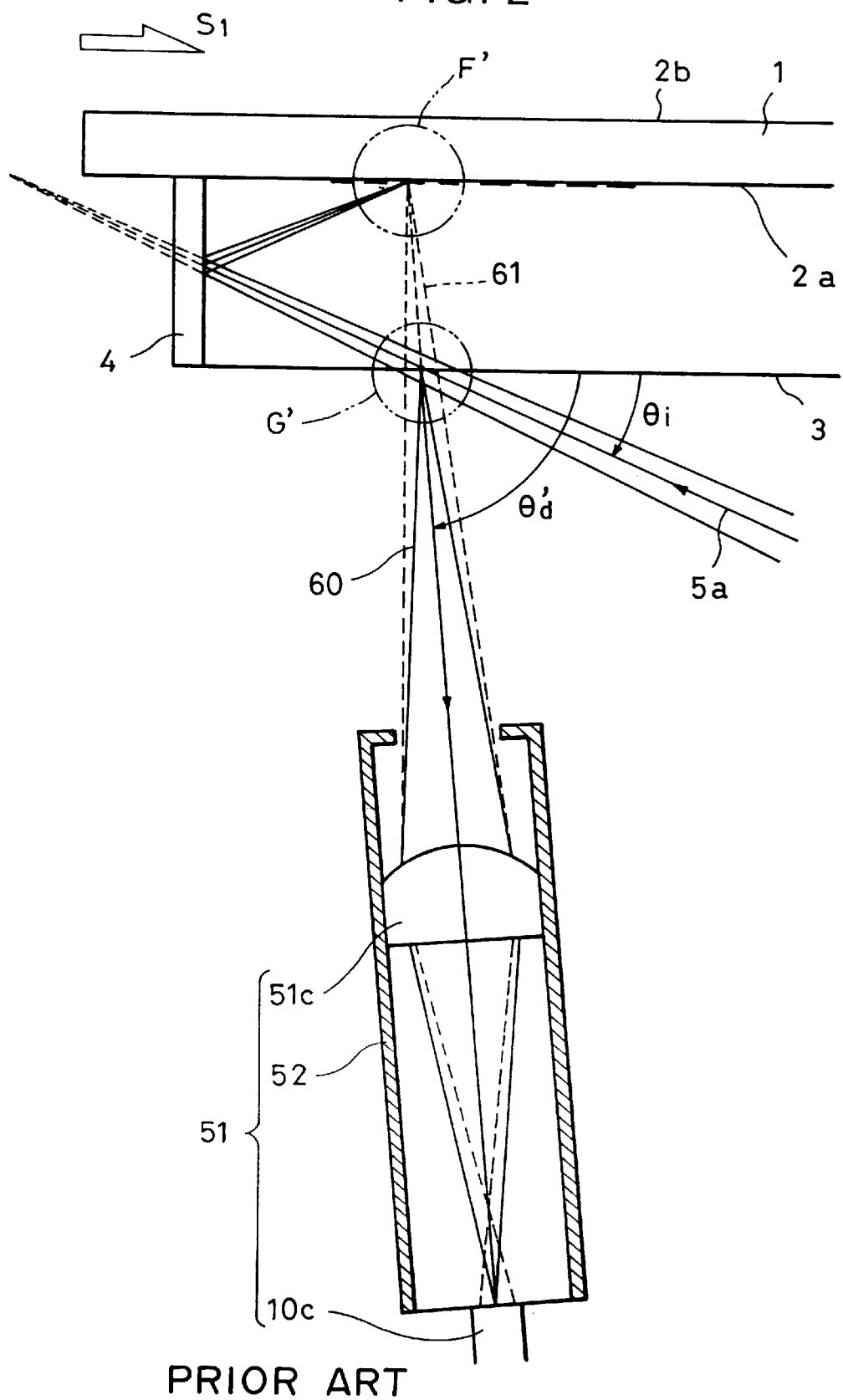
FIG. 2 is a diagram showing a problem with the apparatus shown in FIG. 1.
Figure 3:
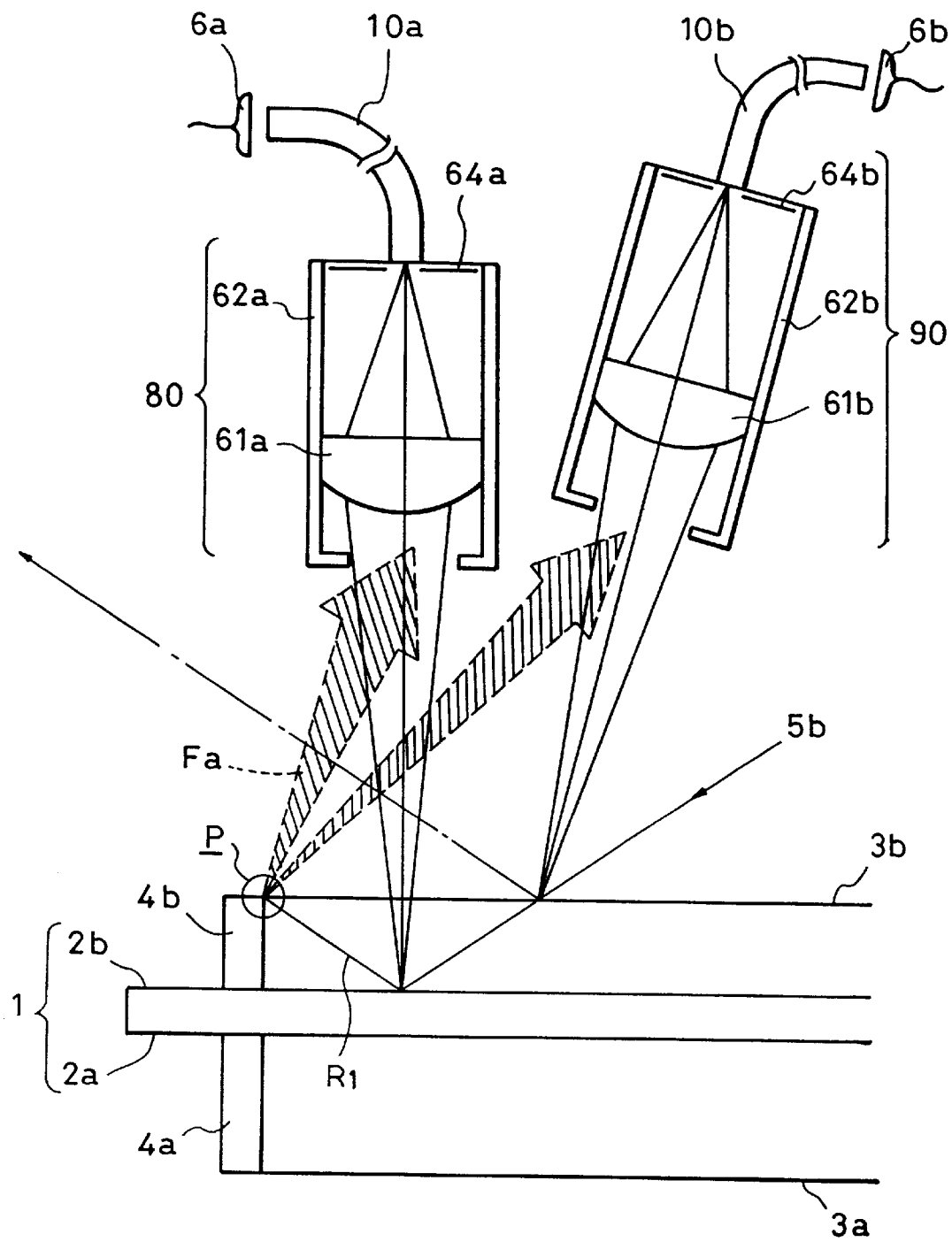
FIG. 3 is a diagram showing another problem with the conventional foreign particle examination apparatus.
Figure 4:
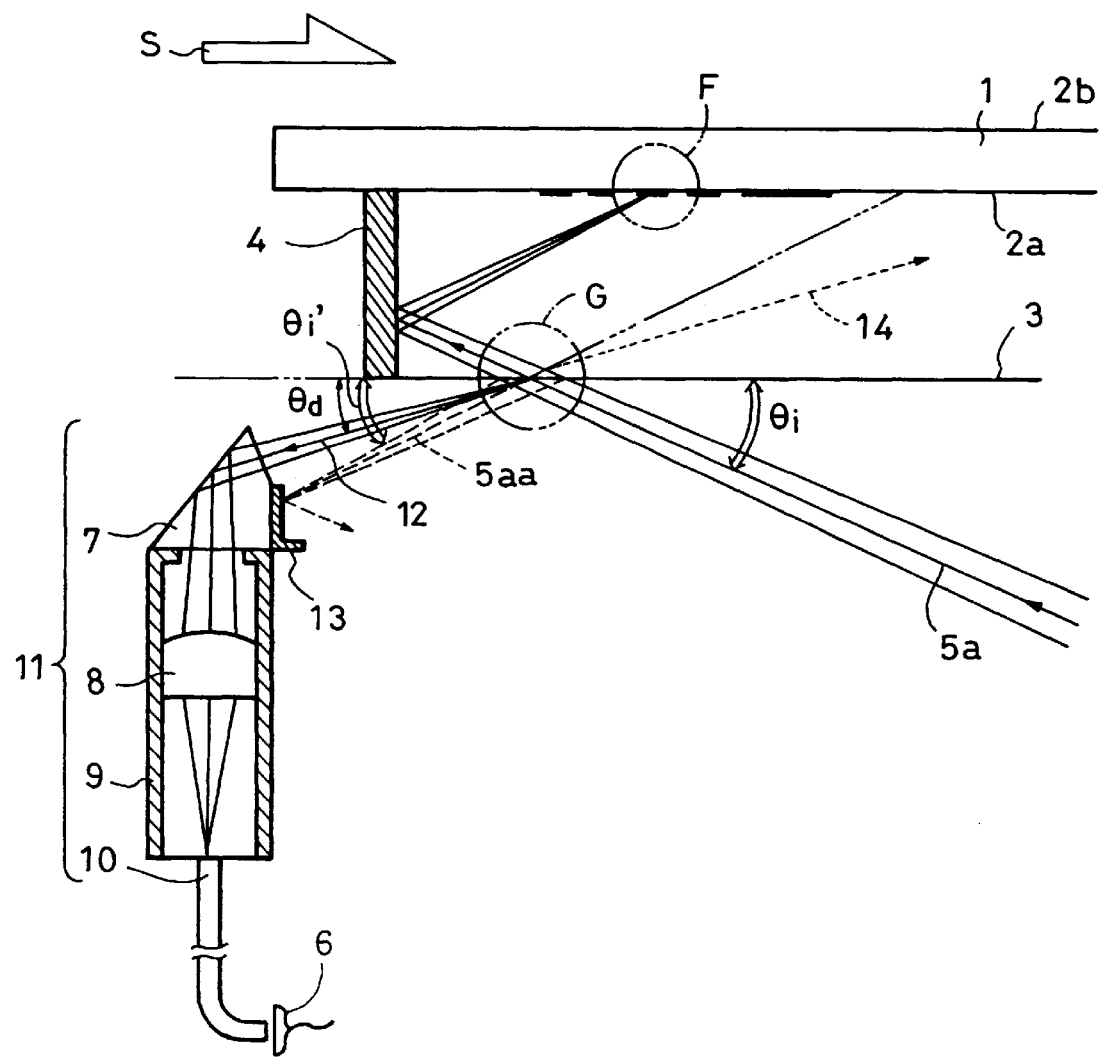
FIG. 4 is a schematic diagram of an apparatus in accordance with an embodiment of the present invention.
Figure 9:
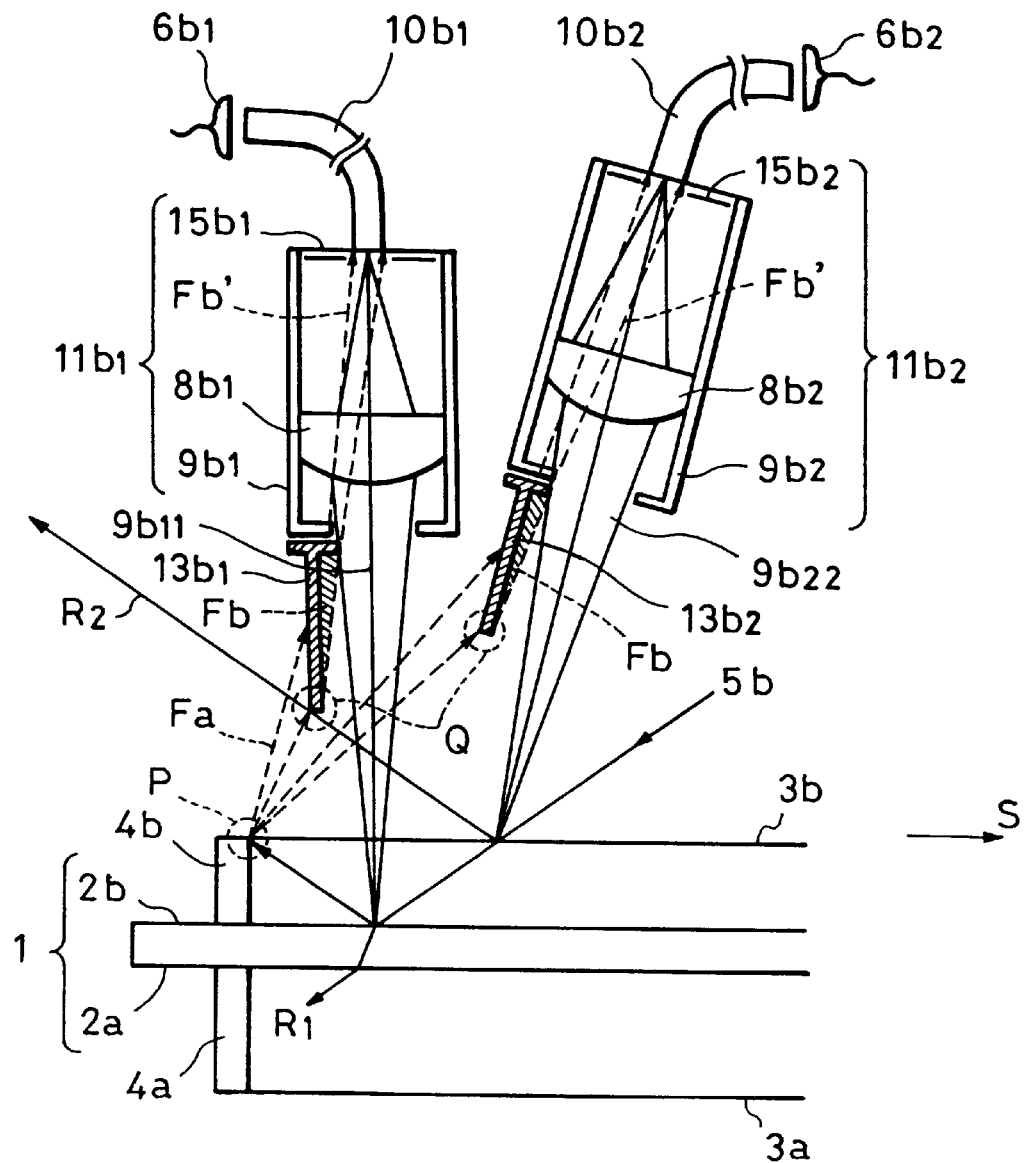
Figure 10:
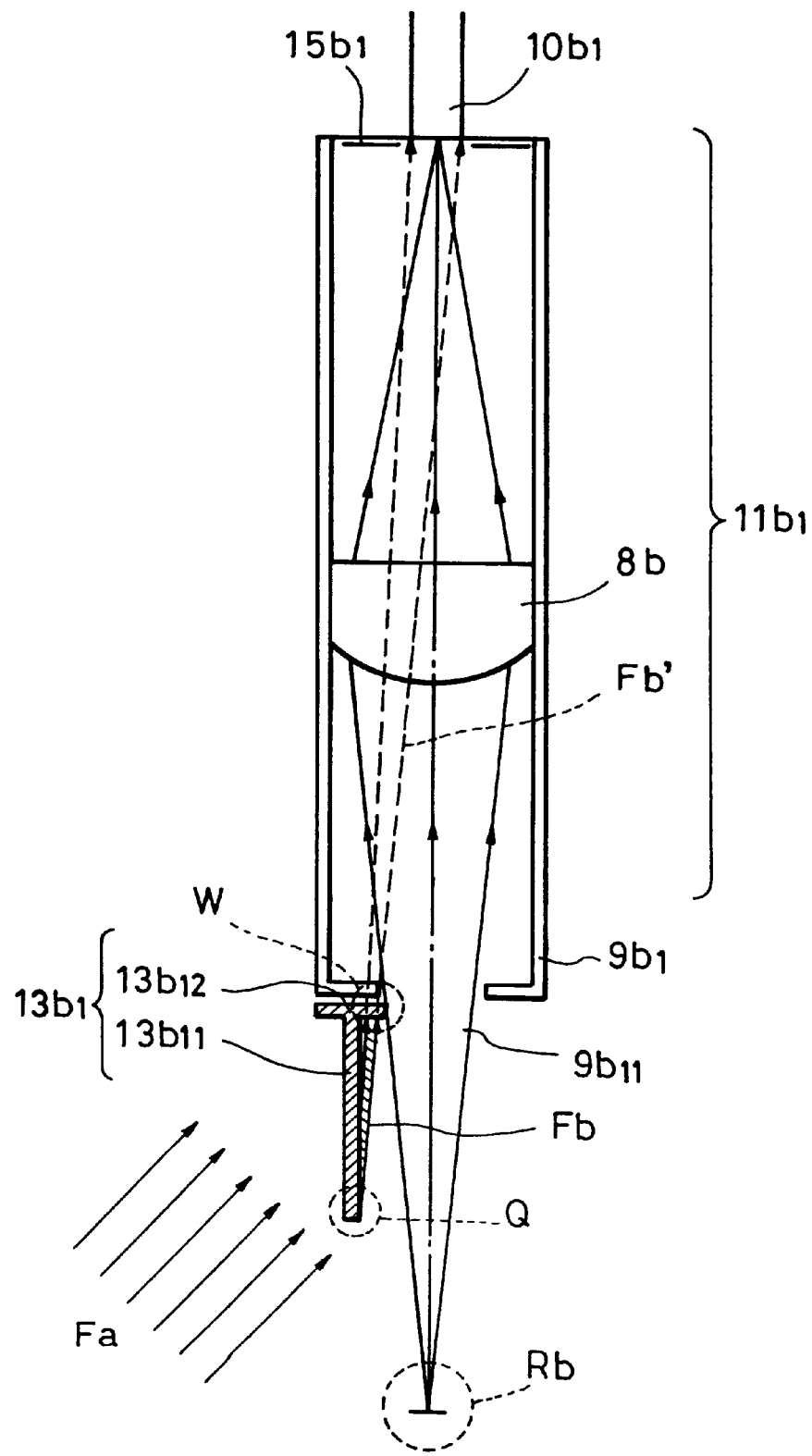
Figure 11:
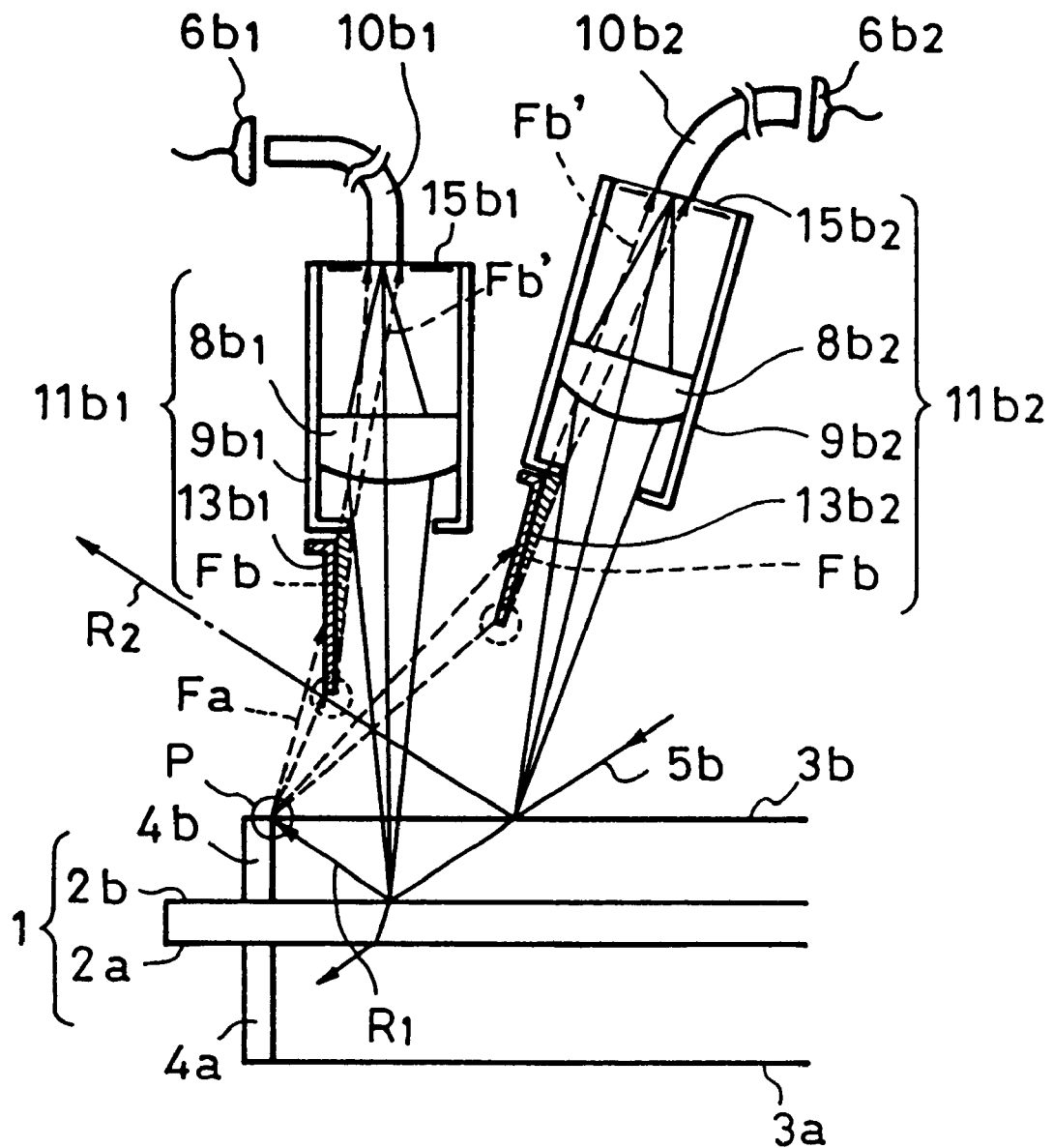
Figure 12:
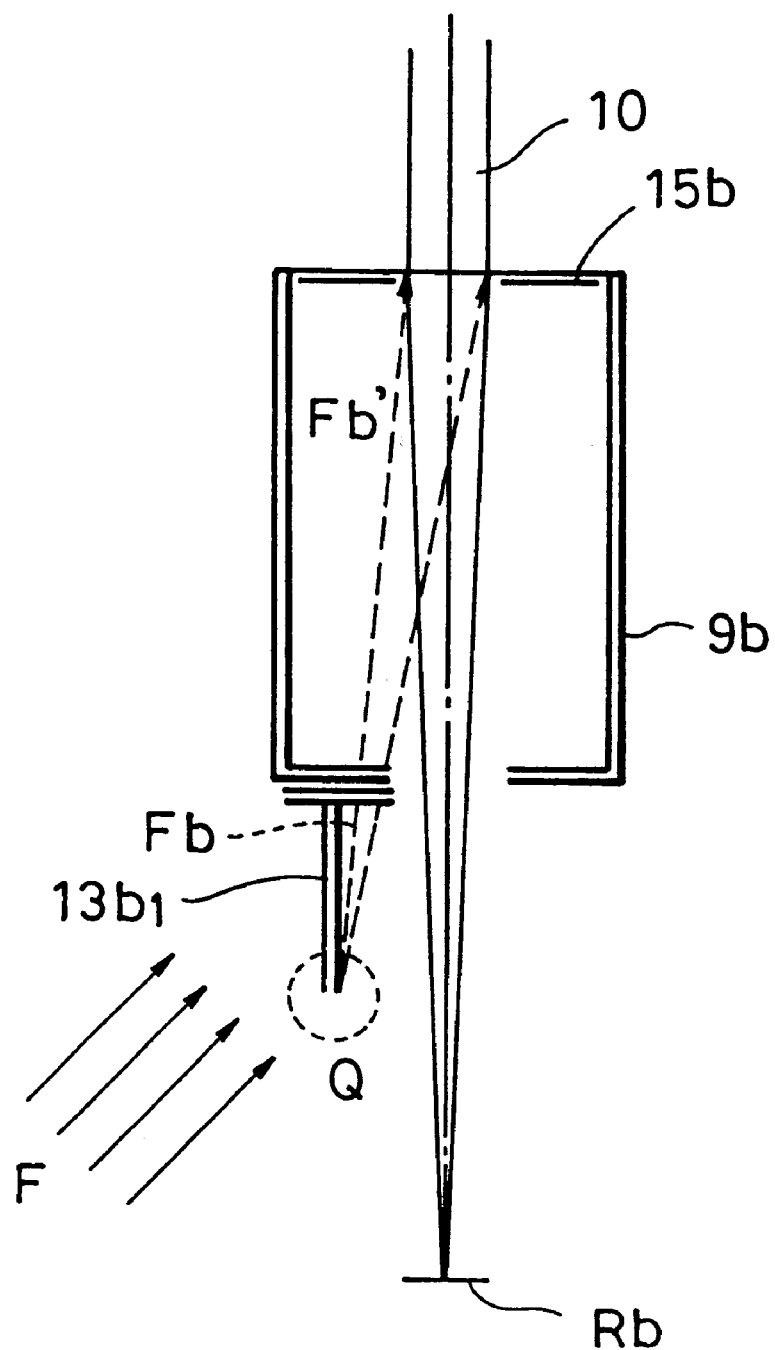
Figure 13:
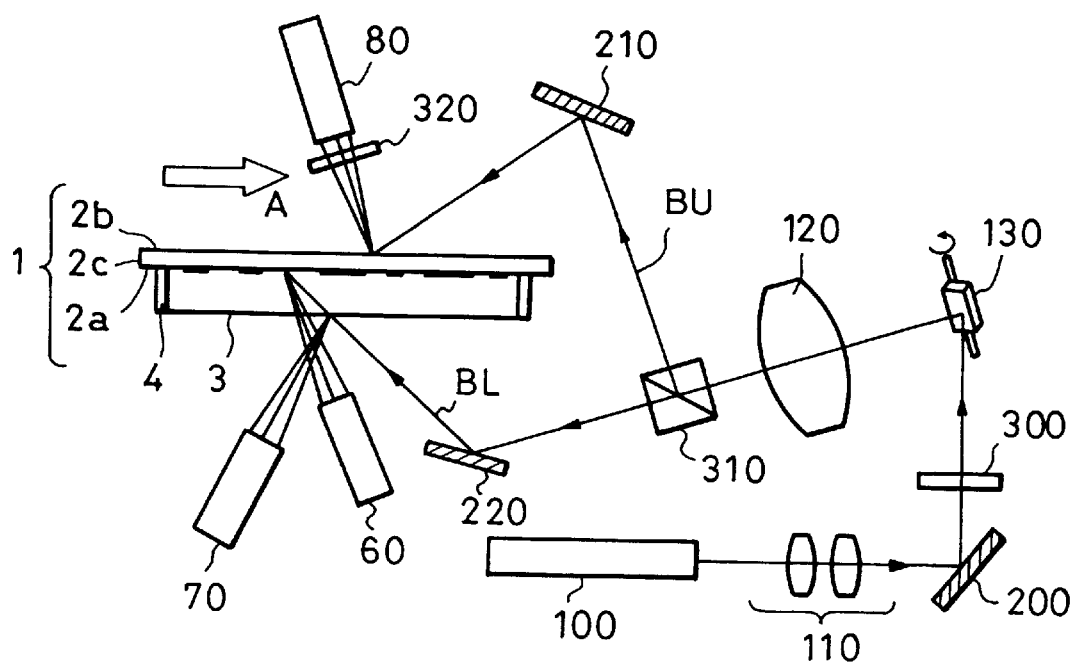
Figure 14:
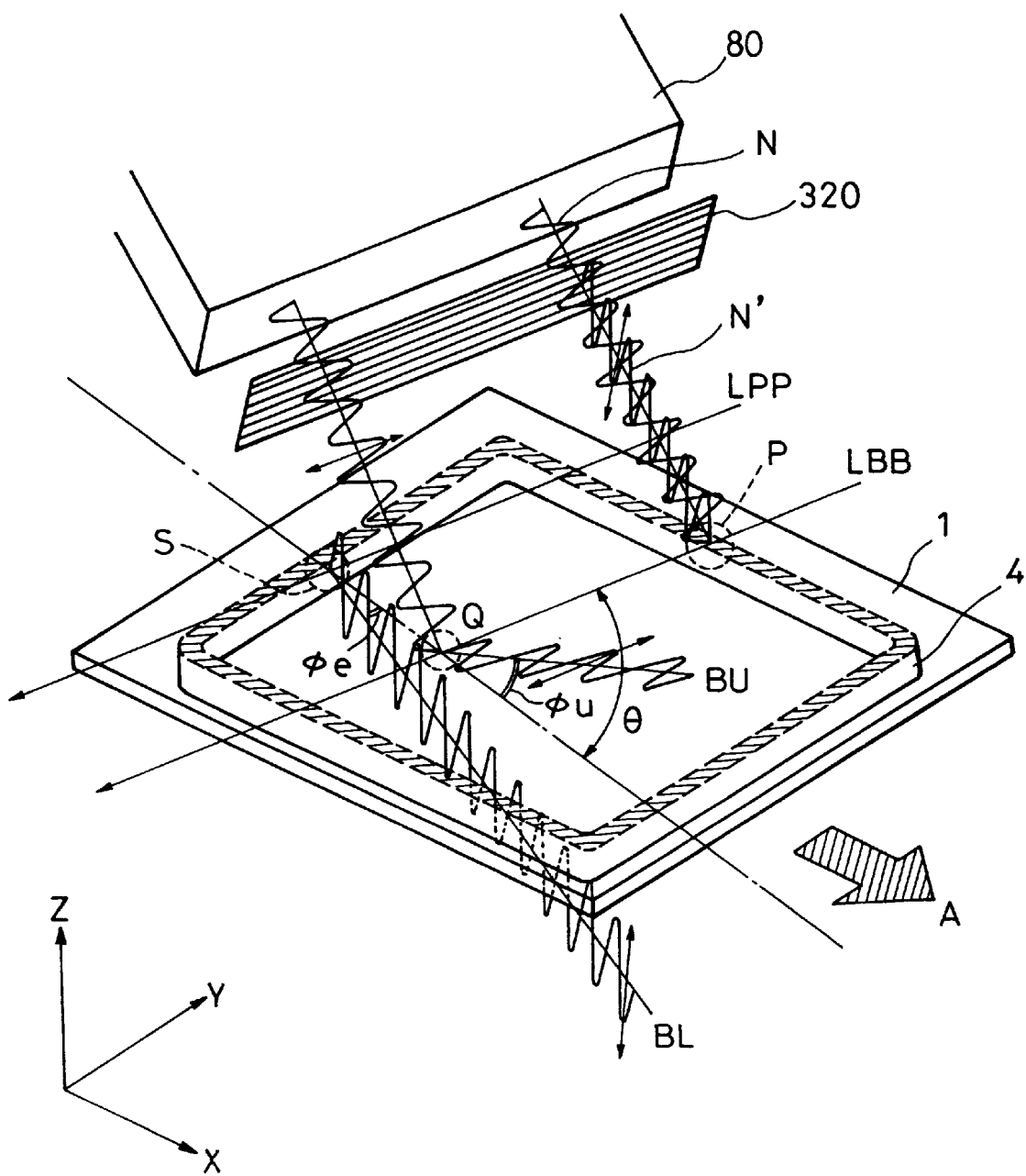

FIGS. (8A) and 8(B) are a cross-sectional view and a plan view of another example of a modification of the apparatus shown FIG. 4;

FIG. 9 a diagram of an apparatus in accordance with another embodiment of the present invention;

FIG. 10 is an enlarged diagram of the light receiving system of the apparatus shown in FIG. 9;

FIG. 11 is a diagram of an example of a modification of the apparatus shown in FIG. 9;

FIG. 12 is a diagram of another example of a modification of the apparatus, shown in FIG. 9;

FIG. 13 is a schematic diagram of an apparatus in accordance with a further embodiment of the present invention;

FIG. 14 is a diagram of a function of the apparatus shown in FIG. 13; and

Figure 15:
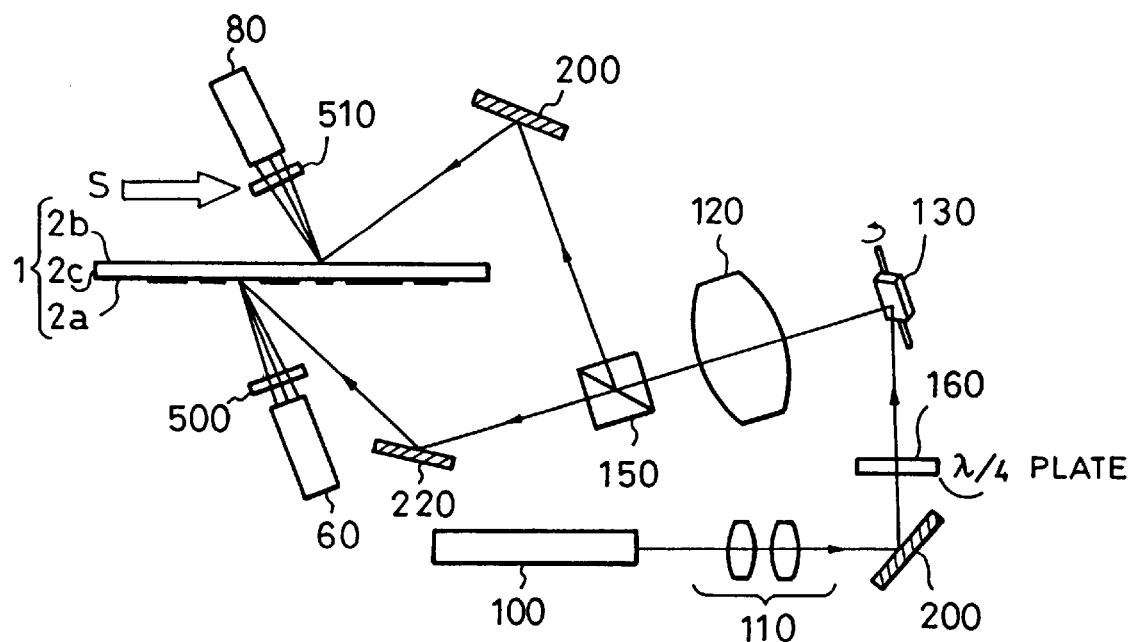

FIG. 15 is a schematic diagram of an example of a modification of the apparatus shown in FIG. 13.

DESCRIPTION OF THE PREFERRED EMBODIMENTS

Figure 5:
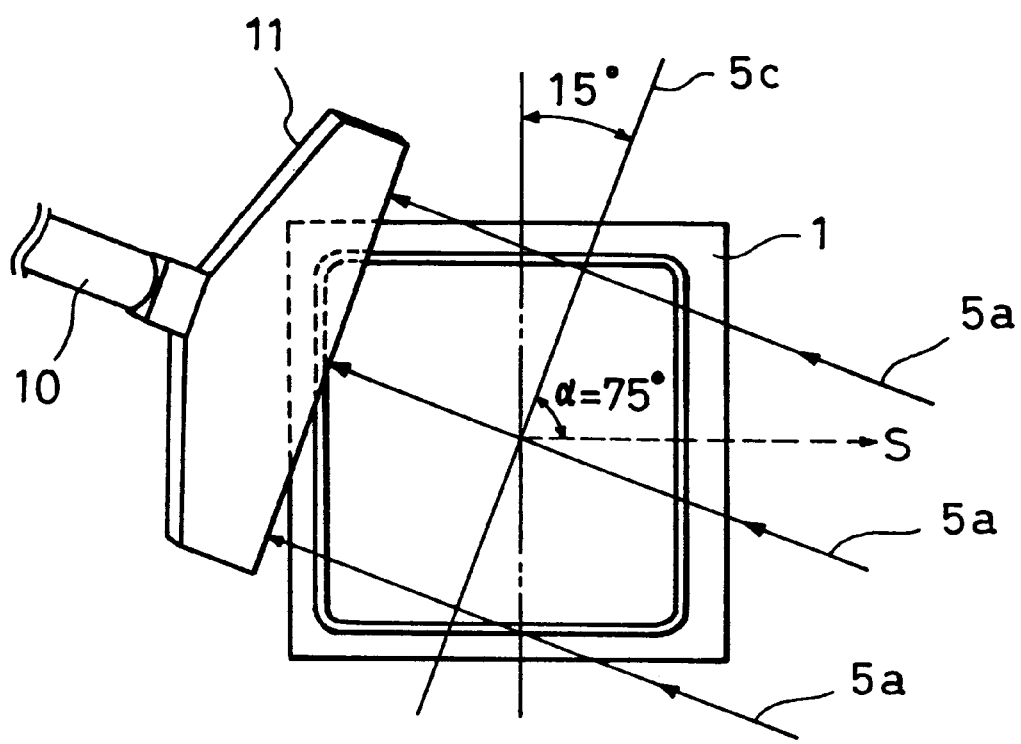
FIG. 5 is a schematic plan view of the apparatus shown in FIG. 4.

FIG. 4 is a schematic diagram of an essential portion of a first embodiment of the present invention. In FIG. 4 are illustrated, as examples of examination means, a light detection means 11 for detecting scattered light from a surface 3 of a pellicle (foreign particle protective film) to be examined, and a light beam 5a emitted from an irradiation means (not shown) to examine the pellicle surface 3 and a substrate surface 2a of a reticle 1 on which a device pattern is formed. Another similar light detection means and another similar light beam (irradiation means) are also provided with respect to other examined surfaces (2a, 2b) in this embodiment, although they are not shown in FIG. 4. A surface 2b is a blank surface. FIG. 5 is a schematic diagram of the reticle 1 and other members seen from underneath. The apparatus shown in FIG. 4 is used alone or by being incorporated in a projection exposure apparatus for manufacturing a device.

As illustrated, the incident beam 5a is moved for scanning in a direction substantially perpendicular to the projected plane of FIG. 4 while being set at an incident angle θi to the reticle 1 and the pellicle surface 3 and being focused on the substrate surface 2a of the reticle 1. This scanning is performed by using a scanning device such as a polygon mirror provided in the irradiation means.

More specifically, as shown in FIG. 5, the scanning is such that an angle α, between a scanning direction 5c of the beam 5a and a direction S in which a movable stage, on which the reticle 1 is mounted, is moved by an unillustrated drive means, is 75 degrees. The stage is moved in the direction of the arrow S so that the entire surface of the reticle 1 (pellicle surface 3) is scanned with the light beam 5a. Preferably, the angle α satisfies the relation $65° < α < 85°$.

During this scanning, the existence or non-existence of scattered light from the substrate surface 2a is detected by another light detection means (not shown) to determine whether any foreign particle, i.e, a dust particle or the like, is attached to the substrate surface 2a. When the reticle 1 is scanned with the beam 5a, the pellicle surface 3 provided below the lower surface 2a of the reticle 1 is also scanned with the same light beam. If at this time a foreign particle is attached in a region G on the pellicle surface 3, scattered light is caused at the region G as the beam 5a passes therethrough.

The light detection means 11 detects scattered light caused at the region G. A light receiving (photodetector) 6 detects scattered light led through the light detection means 11 and an optical fiber 10. A light shield plate 13 prevents noise light from entering a prism mirror 7.

In this embodiment, an angle θd of an optical axis 12 (light receiving direction) of the light detection means 11 for examining the pellicle surface 3 to the surfaces 2a and 3 is smaller than a reflection angle θi' (θi'=θi) to the pellicle surface 3 of a reflection light beam 5aa caused by regular reflection of the incident beam 5a on the pellicle surface 3, as shown in FIG. 4. That is, the angle θd is read out to satisfy:

$$0 < \theta d < \theta i'. \quad (1)$$

Only scattered light caused at the region G is condensed by a cylindrical lens 8 through the prism mirror 7 constituting the light detection means to be imaged on an end surface of the optical fiber 10. The apparatus of this embodiment is arranged with the prism mirror 7 so that the overall size is effectively reduced.

That is, in accordance with this embodiment, relating factors are set so that the conditional equation (1) is satisfied, that is, when a region F of the substrate surface 2a is irradiated with the light beam 5a reflected by the pellicle frame 4, the region F does not intersect a light receiving optical axis 14 of the light detection means 11. Scattered light caused at the region F of the reticle 1, acting as a strong noise source, is thereby prevented from entering the light detection means 11.

Also, in this embodiment, scattered light is detected in a forward direction at an angle of about 40° to the direction of traveling of the incident beam 5a such that stronger scattered light can be obtained.

Figure 6:
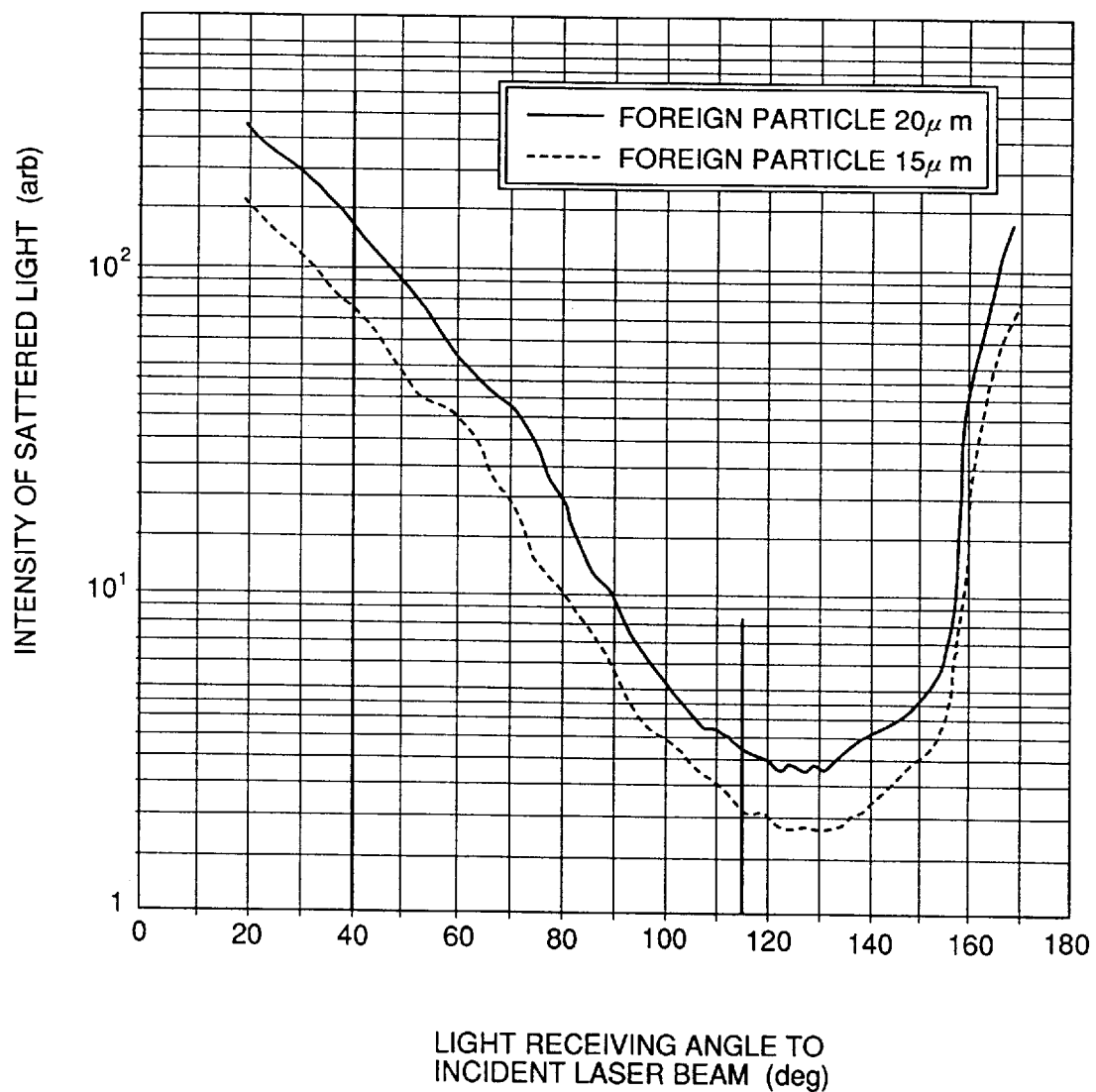
FIG. 6 is a graph showing the relationship between the light receiving angle and the intensity of scattered light.

FIG. 6 is a graph of scattered light distribution characteristics of fine particles in accordance with the Mie's scattering theory.

In the direction of detection in accordance with this embodiment, the intensity of obtained scattered light with respect to, for example, a 15 μm foreign particle is about 30 times greater than that in the case of a detection in a forward direction at about 115°.

In this embodiment, as described above, scattered light (noise light) other than that from the examination target surfaces is prevented from entering the light detection means, thereby ensuring that the existence or non-existence of a foreign particle or the like, which is attached to the examined surface, can be detected with high accuracy.

Figure 7A:
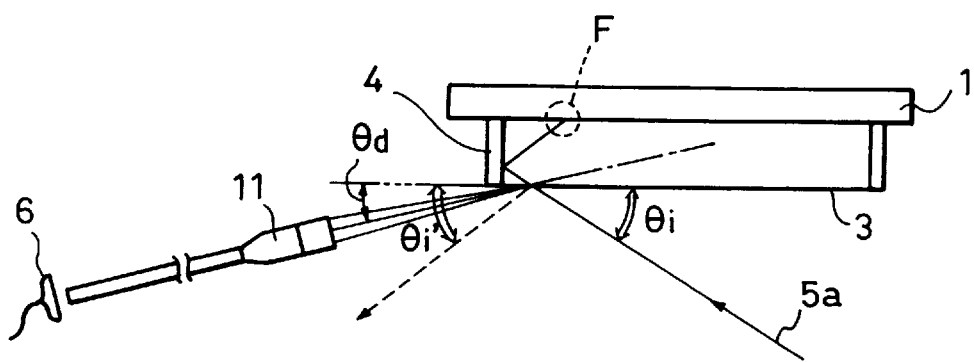
FIGS. 7(A) and 7(B) are cross-sectional view and a plan view of an example of a modification of the apparatus shown in FIGS. 4.
Figure 7B:
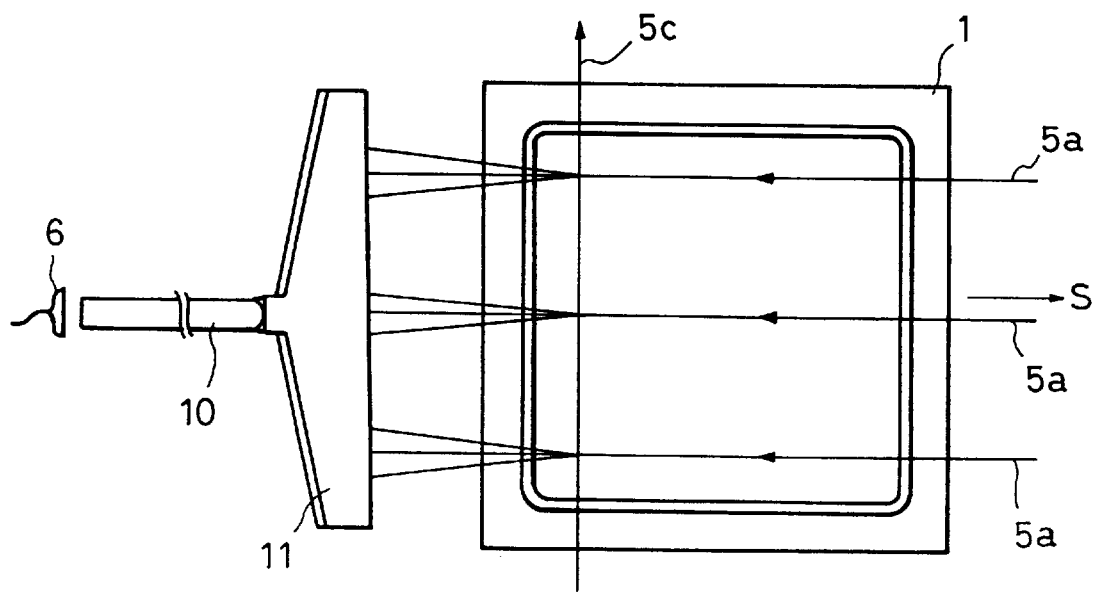

FIGS. 7(A) and 7(B) are a cross-sectional view and a plan view of an essential portion of a second embodiment of the present invention.

This embodiment differs from the first embodiment shown in FIG. 4 in that when a surface of reticle 1 is scanned with light beam 5a, an optical scanning direction 5c is perpendicular to a direction S of movement of the stage. Except for this, the second embodiment has the same construction and effect as those of the first embodiment.

Figure 8A:
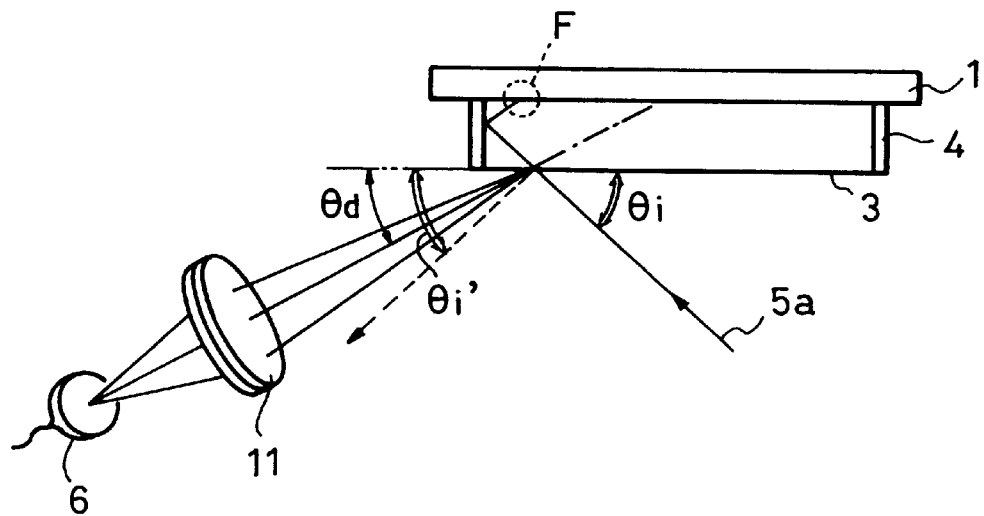
Figure 8B:
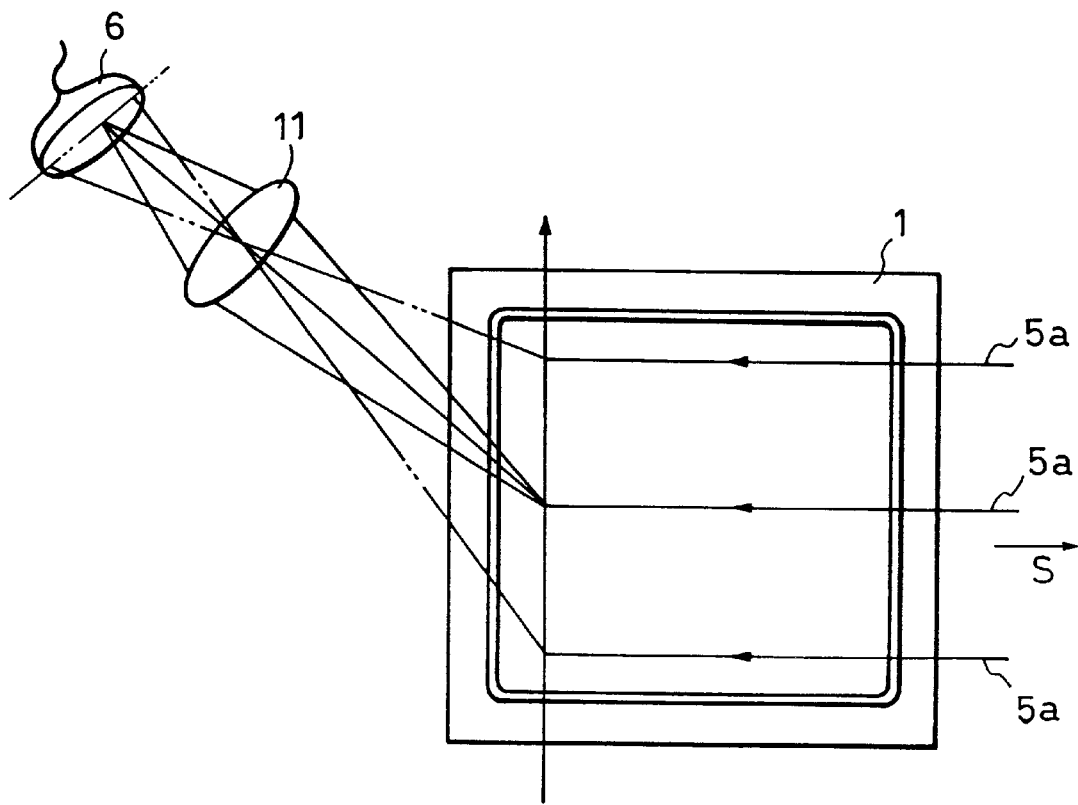

FIGS. 8(A) and 8(B) are diagrams of an essential portion of a third embodiment of the present invention.

This embodiment differs from the first embodiment shown in FIG. 4 in that a light receiving direction of light detection means 11 deviates from a cross section of reticle 1 parallel to light beam 5a incident upon the reticle 1. Except for this, the second embodiment has the same construction and effect as those of the first embodiment.

FIG. 9 is a schematic diagram of an essential portion of a fourth embodiment of the present invention. The apparatus of the fourth embodiment is also used alone or by being incorporated in a projection exposure apparatus for manufacturing a device.

In FIG. 9 are illustrated, as examples of detection means, light detection means 11b1 and 11b2 for detecting scattered light from a blank surface (examined surface) 2b of a reticle 1 and a pellicle surface (examined surface) 3b provided over the blank surface 2b, respectively.

In this embodiment, a light beam 5b from an unillustrated irradiation means is moved in a direction perpendicular to the projected plane of FIG. 9 by a scanning mechanism to scan the pellicle surface 3b and the blank surface 2b in a direction substantially perpendicular to the projected plane of FIG. 9. A stage (not shown) on which the reticle 1 is mounted is moved in the direction of arrow S by an unillustrated drive means so that the entire areas of the surface of the reticle 1 and the pellicle surface 3 are scanned with the light beam 5b. If a foreign particle, i.e., a dust particle or the like, is attached to the examined surface (blank surface 2b and/or pellicle surface 3b), the light beam 5b is scattered by the foreign particle. Also in this embodiment, the arrangement is such that the angle α between the light beam scanning direction and the direction of arrow S (the direction of stage movement) on the examined surface satisfies the relation 65°<α<85°.

Under these conditions, the light detection means 11b1 and 11b2 detect scattered light from the blank surface 2b and the pellicle surface 3b (having an intensity of about $10_{-6}$ if the intensity of light beam 5b is 1). Signals from the light detection means 11b1 and 11b2 are used to determine whether any foreign particle exists on the blank surface 2b and the pellicle surface 3b.

In this embodiment, light shield plates 13b1 and 13b2 having a suitable shape are provided as members partially defining light receiving apertures 9b11 and 9b22 of the light detection means 11b1 and 11b2 to prevent scattered light (noise light) other than that from the examination target surfaces 2b and 3b from passing through the light receiving apertures 9b11 and 9b22 to be received by light receiving elements 6b1 and 6b2.

If light beam 5b is reflected by the blank surface 2b so as to travel to an edge P of a pellicle frame 4b, it is scattered by the edge P. Scattered light Fa from the edge P (having an intensity of about $10_{-3}$ to $10_{-4}$ if the intensity of light beam 5b is 1) may pass through the light receiving apertures 9b11 and 9b22 and stops 15b1 and 15b2 of the light detection means 11b1 and 11b2 to be received by the light receiving elements 6b1 and 6b2 as noise, i.e., a cause of a reduction in the foreign particle detection accuracy.

In accordance with this embodiment, therefore, the light shield plates 13b1 and 13b2 are provided on or beside the light receiving apertures 9b11 and 9b22 of the light receiving means 11b1 and 11b2 to intercept scattered light (noise light) Fa.

FIG. 10 is an enlarged diagram of the light detection means 11b1 and the light shield plate 13b1 provided beside (near) the light receiving aperture 9b11. In FIG. 10, a reference symbol Rb indicates a point at which light beam 5a is incident upon the blank surface 2b of the reticle 1.

While noise light Fa is intercepted by the light shield plate 13b1, a part of noise light Fa may be scattered by a projecting portion Q of a first light shield portion 13b11 to cause secondary scattered light Fb (having an intensity of about $10_{-4}$ to $10_{-6}$) which passes through the light receiving aperture 9b11.

In this embodiment, therefore, a second light shield portion 13b12 is provided to prevent secondary scattered light Fb from the projecting portion Q from passing through the light receiving aperture 9b11. The light shield plate 13b1 is formed of the first and second light shield portions 13b11 and 13b12 so as to have a T-shape in a cross section parallel to the light beam 5b entering the light receiving aperture 9b11. That is, the light shield plate 13b1 is formed so as to have a T-shaped cross-sectional configuration such that the projecting portion Q cannot be viewed from the aperture of the stop 15b1 as along dotted lines shown in FIG. 10.

The light shield plate 13b1 has been described as a member formed integrally of the first and second light shield portions 13b11 and 13b12. However, members corresponding to these shield portions may be formed independently.

In this embodiment, the light shield plate 13b2 provided on or beside the light receiving aperture 9b22 has the same shape and effect as the light shield plate 13b1.

In this embodiment, the thus-formed light shield plates 13b1 and 13b2 are used to prevent scattered light other than that from the examination target surfaces, e.g., scattered light traveling directly from the pellicle frame 4b and secondary scattered light from the projecting portion of the first light shield portion, from entering the light receiving elements of the light detection means. The accuracy with which the existence or non-existence of foreign particles on the examination target surfaces is detected is thereby satisfactorily maintained. In this embodiment, the light detection means 11b1 may be disposed obliquely with respect to the blank surface 3b. Also in such a case, a similar improvement can be achieved.

FIG. 11 is a schematic diagram of an essential portion of a fifth embodiment of the present invention. The apparatus of the fifth embodiment also is used alone or by being incorporated in a projection exposure apparatus for manufacturing a device.

In this embodiment, a first light shield member 13b11 is formed so as to be L-shaped in section and is disposed at a distance from light receiving aperture 9b11, and a part of the portion defining light receiving aperture 9b11 of lens barrel 9b1 of light detection means 11b1 is utilized as a second light shield member 13b12. The first light shield member 13b11 and the second light shield member 13b12 are formed so as to be generally T-shaped in section as a whole.

Scattered light other than that from the examination target surfaces, e.g., scattered light from the pellicle frame and secondary scattered light from the projecting portion Q of the first light shield member 13b11, is thereby prevented from entering the light receiving elements of the light detection means. In other respects, the construction of this embodiment is the same as that of the fourth embodiment shown in FIG. 9.

In the above-described embodiments, each of the cylindrical lenses 8b1, 8b2 which is one constituent of each light detection means 11b1, 11b2 may be removed. For example, in the fourth embodiment shown in FIG. 9, the light shield plate 13b1 may be formed so as to have a T-shaped cross-sectional configuration such that the projecting portion Q cannot be viewed from the aperture of the stop 15b, as shown in FIG. 12.

FIG. 13 a schematic diagram of essential components of a sixth embodiment of the present invention, and FIG. 14 is a perspective view of an essential portion of the system shown in FIG. 13. The apparatus of the sixth embodiment is also used alone or by being incorporated in a projection exposure apparatus for manufacturing a device.

A component 100 is a light source, such as a laser device, which emits a beam of linearly polarized light. The beam of linearly polarized light from the light source 100 is expanded in diameter by a beam expander (afocal converter) 110, reflected by a mirror 200, converted into a beam of circularly polarized light by a $\lambda/4$ plate 300 and thereafter incident upon a scanning mirror 130 formed of a rotating mirror (polygon mirror) or a vibrating mirror (galvanomirror).

The beam from the scanning mirror 130 travels through an f-θ lens 120 having an f-θ characteristic and is split by a polarizing beam splitter 310 into two beams of linearly polarized light, i.e., reflected light BU and transmitted light BL polarized in directions orthogonal to each other. The light beam BL, transmitted through the polarizing beam splitter 310, travels via a mirror 220 to be incident upon an examined object 1 obliquely from below in a P-polarized state. The light beam BU, reflected by the polarizing beam splitter, travels via a mirror 210 to be incident upon the examined object obliquely from above in an S-polarized state.

In this embodiment, a reticle which is an examined object 1 has a substrate 2c and a pellicle surface 3 provided on the circuit pattern 2a side of the substrate. A reverse surface (upper surface, blank surface) 2b, and obverse pattern surface 2a of the substrate 2c and the pellicle surface 3 are surfaces to be examined. The examined object 1 can be moved in the direction of arrow A by an unillustrated drive means.

Light detection means 60, 70, and 80 are set so as to be focused on the examined surfaces 2a, 3, and 2b, respectively. The light detection means 60, 70, and 80 have light receiving lenses and unidimensional sensors having light receiving surfaces elongated in a direction perpendicular to the projected plane of FIG. 13.

The light detection means 60, 70, and 80 are placed in regions deviating from the optical paths of reflected light and transmitted light formed directly from the light beams BU and BL and serve to detect scattered light from the examined surfaces. An analyzer (polarizing plate) 320 is provided at an aperture of the light detection means 80 to transmit only a beam of S-polarized light while intercepting P-polarized light, which is the same as the light beam BL.

In this embodiment, the scanning mirror 130 is rotated or vibrated to scan the examined object 1 with the light beams from the light source 100, i.e., the S-polarized light beam BU from above and the P-polarized light beam BL from below simultaneously along scanning lines LBB and LPP (FIG. 14) in a direction perpendicular to the projected plane of FIG. 13. Simultaneously, the examined object 1 is moved in the direction of arrow A to two-dimensionally scan the examination target surfaces with the light detection means 80, 70, and 60 provided in correspondence with the examined surfaces to detect scattered light from foreign particles or dust particles attached to the surfaces.

The construction of each of the light detection means 80, 70, and 60 is the same as that of the light detection means 11 of the above-described embodiment.

In this embodiment, P-polarized light BL is supplied from the pattern surface 2a side, and scattered light in a randomly polarized state from the examined surfaces 2a and 3 is detected by the light detection means 60 and 70. Flare light (noise light) from a pellicle frame bonding surface caused from the P-polarized light beam BL from below is simultaneously scattered on the blank surface 2b side in a state of being substantially randomly polarized.

The analyzer 320 is therefore provided at the aperture of the light detection means 80 on the blank surface 2b side to transmit only S-polarized light while preventing flare light in other polarized states from reaching the light detection means 80. If the scattered light from the pellicle frame bonding surface 4 is N' and the flare light traveling to the light detection means 80 is N, where substantially N<N'/2.

That is, the analyzer 320 is used so that substantially no scattered light from the pellicle frame bonding surface is received by the light detection means 80. The S-polarized light beam BU is incident upon the examined surface 2b above the examined object 1. It is known that the rate at which scattered light S, from a foreign particle attached to the examined surface 2b, is disturbed is small and that almost all components of the scattered light S are S-polarized components.

Therefore, the analyzer 320 for transmitting only S-polarized light is provided at the aperture of the light detection means 80 as described above to allow passage of S-polarized light. The influence of flare light caused by the P-polarized light BL under the examined object is thereby reduced. Therefore, scattered light from a foreign particle on the examined surface 2b is detected effectively, i.e., at a high S/N ratio.

Thus, in this embodiment, the polarized states of the upper light beam LBB and the lower light beam LPP are set so as to be different from each other, and a polarizing plate is provided at one of the two corresponding light detection means, thereby making it possible to scan examination target surfaces with light beams without any considerable influence of flare light from a pellicle frame or the like and to efficiently detect scattered light from the target surfaces. The surface states of the examined surfaces are thereby detected two-dimensionally and accurately.

Also in this embodiment, the angle α between the light beam scanning direction and the direction of movement of the examined object on the examined surfaces is set so as to satisfy $65°<\alpha<85°$, thereby enabling scattered light from the examination target surfaces to be effectively detected so that the examination accuracy is improved.

In this embodiment, the need for λ/4 plate 300 may be eliminated by using a polarizing laser as light source 100.

FIG. 15 is a schematic diagram of essential components of a seventh embodiment of the present invention. The apparatus of the seventh embodiment also is used alone or by being incorporated in a projection exposure apparatus for manufacturing a device.

In this embodiment, a reticle 1 having no pellicle is used as an examined object. That is, only two surfaces, i.e., a pattern surface 2a and a blank surface 2b of a substrate 2c are examined surfaces. If no pellicle surface is provided on the pattern surface 2a side, a beam of S-polarized light is incident upon the pattern surface 2a, and an analyzer 500, through which S-polarized light can pass, is provided at light detection means 60. Only scattered light from foreign particles caused from S-polarized light on the pattern surface is detected with the light detection means 60.

The blank surface 2b is irradiated with a beam of P-polarzed light polarized in a direction perpendicular to the direction of polarization of S-polarized light, and an analyzer 510, through which P-polarized light can pass, is provided at light detection means 80. Only scattered light from foreign particles caused from P-polarized light on the blank surface 2b is detected with the light detection means 80.

Thus, in this embodiment, the influence of flare light from portions other than the examination target surfaces is reduced to improve the accuracy with which the surface states of the examined surfaces are determined.

According to the sixth and seventh embodiments, a surface state examination apparatus is achieved in which light beams incident upon an examined object from above and from below are set in suitable polarized states so that scattered light from foreign particles or dust particles attached to examined surfaces can be detected efficiently, and which is therefore capable of examining the surface states of a plurality of examined surfaces with high accuracy.

While the present invention has been described with respect to what presently are considered to be the preferred embodiments, it is to be understood that the invention is not limited to the disclosed embodiments. To the contrary, the present invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method for inspecting foreign particles on a pellicle, the method comprising the steps of:

directing a light beam to be obliquely incident upon a pattern surface of a reticle through the pellicle stretched on a pellicle frame, which is placed on the pattern surface;

moving the obliquely incident light beam and the reticle relative to each other; and detecting, by a detector, a scattered light from the pellicle traveling along a detection optical axis to inspect foreign particles on the pellicle, wherein a first angle formed between the detection optical axis of the detector and a pellicle surface is smaller than a second angle formed between a specularly reflected light of the obliquely incident light beam reflected by the pellicle surface and the pellicle surface, both the first and the second angles being measured from a side of the pellicle surface closest to the specularly reflected light, such that when the light beam is reflected by the pellicle frame and irradiates the pattern surface, a scattered light caused at the pattern surface is thereby prevented from entering the detector.

2. A method according to claim 1, wherein the scattered light from the pellicle is a forwardly-scattered reflected light.

3. A method according to claim 1, further comprising the step of detecting scattered light from the pattern surface to detect foreign particles on the pattern surface.

4. A method according to claim 1, wherein an angle α between the direction in which the obliquely incident light is moved and the direction in which the reticle is moved satisfies $65°<\alpha<85°$.

5. A method according to claim 1, wherein the light beam is a laser beam.

* * * * *

UNITED STATES PATENT AND TRADEMARK OFFICE
CERTIFICATE OF CORRECTION

PATENT NO. : 5,963,316
DATED : October 5, 1999
INVENTOR(S) : SEIYA MIURA, ET AL.

It is certified that error appears in the above-identified patent and that said Letters Patent is hereby corrected as shown below:

COLUMN 1
   Line 34, "2b" should read --2a--.

COLUMN 4
   Line 1, "alanyzer," should read --analyzer,--.
   Line 10, "alanyzer" should read --analyzer--.
   Line 25, "alanyzer" should read --analyzer--.

COLUMN 5
   Line 66, "FIG. 6" should read --¶ FIG.6--.

COLUMN 6
   Line 1, "are" should read --are a--.
   Line 7, "a" should read --is a--.

COLUMN 8
   Line 28, "$10_{-6}$" should read --$10^{-6}$--.
   Line 44, "$10_{-3}$ to $10_{-4}$" should read --$10^{-3}$ to $10^{-4}$--.
   Line 64, "$10_{-4}$ to $10_{-6}$" should read --$10^{-4}$ to $10^{-6}$--.

UNITED STATES PATENT AND TRADEMARK OFFICE
CERTIFICATE OF CORRECTION

PATENT NO. : 5,963,316
DATED : October 5, 1999
INVENTOR(S) : SEIYA MIURA, ET AL.

It is certified that error appears in the above-identified patent and that said Letters Patent is hereby corrected as shown below:

COLUMN 11

Line 55, "P-polarzed" should read --P-polarized--.

Signed and Sealed this

Seventh Day of November, 2000

Attest:

Q. TODD DICKINSON

Attesting Officer      Director of Patents and Trademarks